*(12)* United States Patent
Lal et al.

(10) Patent No.: US 12,116,353 B1
(45) Date of Patent: Oct. 15, 2024

(54) CRYSTALLINE CHLORO-N-(4-(MORPHOLINOMETHYL) PHENYL)BENZAMIDE AND CRYSTALLINE HYDROCHLORIDE SALT

(71) Applicant: GEN1E LIFESCIENCES INC., Palo Alto, CA (US)

(72) Inventors: Ritu Lal, Palo Alto, CA (US); Adam Galan, Maryville, TN (US); Nathan Larson, Palo Alto, CA (US)

(73) Assignee: GENIE LIFESCIENCES INC., Palo Alto, CA (US)

( * ) Notice: Subject to any disclaimer, the term of this patent is extended or adjusted under 35 U.S.C. 154(b) by 0 days.

(21) Appl. No.: 18/645,972

(22) Filed: Apr. 25, 2024

(51) Int. Cl.
| | | |
|---|---|---|
| *C07D 265/30* | (2006.01) | |
| *A61K 31/5375* | (2006.01) | |
| *A61P 11/00* | (2006.01) | |
| *A61P 25/00* | (2006.01) | |
| *A61P 29/00* | (2006.01) | |
| *A61P 35/00* | (2006.01) | |
| *A61P 37/00* | (2006.01) | |

(52) U.S. Cl.
CPC ........ *C07D 265/30* (2013.01); *A61K 31/5375* (2013.01)

(58) Field of Classification Search
CPC ... C07D 265/30; A61K 31/5375; A61P 11/00; A61P 25/00; A61P 29/00; A61P 35/00; A61P 37/00
See application file for complete search history.

(56) References Cited

U.S. PATENT DOCUMENTS 11,078,171 B2 *  8/2021  Shapiro ............... C07D 307/52
11,286,260 B2     3/2022  Galan et al.

OTHER PUBLICATIONS

Biava et al., Antimycobacterial activity of new ortho-, meta- and para-toluidine derivatives, Il Farmaco, 1999, vol. 54, pp. 721-727.
Biava et al., Synthesis and antimycobacterial activity of new amido derivatives of ortho-, meta- and para-toluidine, Medicinal Chemistry Research, 1998, 8(9), pp. 523-541.
Fang et al., Modulation of mitogen-activated protein kinase attenuates sepsis-induced acute lung injury in acute respiratory syndrome rats, *Molecular Medicine Reports*, 16, 2017, pp. 9652-9658.
MacNee et al., Efficacy and safety of the oral p38 inhibitor PH-797804 in chronic obstructive pulmonary disease: a randomised clinical trial, *Thorax*, 68, 2013, pp. 738-745.

* cited by examiner

*Primary Examiner* — Brenda L Coleman (57) ABSTRACT

Crystalline 4-chloro-N-(4-(morpholinomethyl)phenyl)benzamide, crystalline 4-chloro-N-(4-(morpholinomethyl)phenyl)benzamide hydrochloride, methods of preparing the crystalline compounds, pharmaceutical compositions containing the crystalline compounds, and methods of treatment using the crystalline compounds are disclosed.

15 Claims, 3 Drawing Sheets

CRYSTALLINE CHLORO-N-(4-(MORPHOLINOMETHYL) PHENYL)BENZAMIDE AND CRYSTALLINE HYDROCHLORIDE SALT

FIELD

The invention relates to crystalline 4-chloro-N-(4-(morpholinomethyl)phenyl)benzamide and the crystalline hydrochloride salt, methods of preparing the crystalline compounds, pharmaceutical compositions containing the crystalline compounds, and methods of treatment using the crystalline compounds.

BACKGROUND

Mitogen-activated protein kinases (MAPKs) are serine/threonine protein kinases that process and regulate cellular properties in response to a wide range of extracellular stimuli. These enzymes phosphorylate the OH group of serine or threonine in proteins and play important roles in the regulation of cell proliferation, differentiation, survival, and apoptosis. In mammalian cells, several distinct MAPKs have been identified, including p38 MAPK.

$p^{38}$ MAPK is a class of MAPKs responsive to stress stimuli such as inflammatory cytokines and reactive oxygen species (ROS) and is involved in a wide range of signaling pathways that stimulate different biological functions. For example, p38 MAPK plays an essential role in the regulation of pro-inflammatory signaling networks and in the biosynthesis of cytokines, including tumor necrosis factor-$\alpha$ (TNF-$\alpha$) and interleukin-1$\beta$ (IL-1$\beta$) in immune cells.

Studies have shown that p38 MAPK contributes to the pathogenesis of chronic inflammation, which has led to the identification and development of p38 MAPK inhibitors for treating inflammatory diseases such as rheumatoid arthritis and asthma.

$p^{38}$ MAPK comprises four isoforms ($\alpha$, $\beta$, $\gamma$ and $\delta$). p38$\alpha$ MAPK was the first isoform of p38 MAPK to be identified and was first recognized as a stress-induced kinase that can be activated by lipopolysaccharide (LPS) and inflammatory cytokines. Inhibition of p38 MAPK has been shown to effectively alleviate inflammatory diseases such as rheumatoid arthritis, cardiovascular disease, and inflammatory pain.

Many p38 MAPK catalytic inhibitors are poorly effective and cause toxicity, possibly due to activity against non-inflammatory p38 and loss of p38$\alpha$-dependent counterregulatory responses. p38$\alpha$ MAPK inhibitors that can selectively block certain p38$\alpha$ MAPK functions and preserve critical counterregulatory and homeostatic functions with application for the treatment of inflammatory and oncologic diseases are desired.

4-Chloro-N-(4-(morpholinomethyl)phenyl)benzamide is disclosed in U.S. Publication No. 2020/0331874 A1 with compounds exhibiting p38$\alpha$ MAPK inhibitory activity.

SUMMARY

According to the present invention, a compound is crystalline 4-chloro-N-(4-(morpholinomethyl)phenyl)benzamide hydrochloride.

According to the present invention, a pharmaceutical composition comprises crystalline 4-chloro-N-(4-(morpholinomethyl)phenyl)benzamide hydrochloride and a pharmaceutically acceptable excipient.

According to the present invention, a method of treating a disease in a patient comprises administering to a patient in need of such treatment a therapeutically effective of amount of crystalline 4-chloro-N-(4-(morpholinomethyl)phenyl)benzamide hydrochloride, wherein the disease is selected from cancer, an inflammatory disease, an autoimmune disease, a respiratory disease, and an age-related disease.

According to the present invention methods of inhibiting the p38$\alpha$ MAPK receptor comprise contacting the p38$\alpha$ MAPK receptor with crystalline 4-chloro-N-(4-(morpholinomethyl)phenyl)benzamide hydrochloride.

According to the present invention methods of inhibiting the p38$\alpha$ MAPK receptor in a patient comprise administering to a patient a pharmacologically effective amount of crystalline 4-chloro-N-(4-(morpholinomethyl)phenyl)benzamide hydrochloride.

According to the present invention methods of making 4-chloro-N-(4-(morpholinomethyl)phenyl)benzamide hydrochloride comprises reacting 4-chloro-N-(4-(morpholinomethyl)phenyl)benzamide with hydrochloric acid.

According to the present invention a compound is crystalline 4-chloro-N-(4-(morpholinomethyl)phenyl)benzamide.

According to the present invention a pharmaceutical composition comprises crystalline 4-chloro-N-(4-(morpholinomethyl)phenyl)benzamide and a pharmaceutically acceptable excipient.

According to the present invention methods of treating a disease in a patient comprise administering to a patient in need of such treatment a therapeutically effective of amount of crystalline 4-chloro-N-(4-(morpholinomethyl)phenyl)benzamide, wherein the disease is selected from cancer, an inflammatory disease, an autoimmune disease, a respiratory disease, and an age-related disease.

According to the present invention methods of inhibiting the p38$\alpha$ MAPK receptor comprise contacting the p38$\alpha$ MAPK receptor with crystalline 4-chloro-N-(4-(morpholinomethyl)phenyl)benzamide.

According to the present invention methods of inhibiting the p38$\alpha$ MAPK receptor in a patient comprise administering to a patient a pharmacologically effective amount of crystalline 4-chloro-N-(4-(morpholinomethyl)phenyl)benzamide.

According to the present invention methods of making 4-chloro-N-(4-(morpholinomethyl)phenyl)benzamide comprise: reacting 4-amino benzyl alcohol with 4-chlorobenzoyl chloride to provide 4-chloro-N-(4-(hydroxymethyl)phenyl)benzamide; reacting 4-chloro-N-(4-(hydroxymethyl)phenyl)benzamide with thionyl chloride to provide 4-chloro-N-(4-(chloromethyl)phenyl)benzamide; and reacting 4-chloro-N-(4-(chloromethyl)phenyl)benzamide with morpholine to provide 4-chloro-N-(4-(morpholinomethyl)phenyl)benzamide.

BRIEF DESCRIPTION OF THE DRAWINGS

The drawings described herein are for illustration purposes only. The drawings are not intended to limit the scope of the present disclosure.

DETAILED DESCRIPTION

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Compounds" and moieties disclosed herein include any specific compounds within the disclosed formula. Compounds may be identified either by chemical structure and/or by chemical name. Compounds are named using the ChemDraw Professional 22.2.0.3300 (PerkinElmer Informatics, Inc.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers.

Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

A crystalline compound refers to crystalline compound (1) and/or crystalline compound (2).

"Immediate release" refers to a pharmaceutical composition that releases substantially all of a pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Modified release" pharmaceutical compositions include controlled release formulations, delayed release formulations, extended-release formulations, sustained release formulations, timed release formulations, pulsatile release formulations, and pH-dependent release formulations. These formulations are intended to release a pharmaceutically active ingredient from the pharmaceutical composition at a desired rate and/or at a desired time following oral administration by a patient and/or at a certain location or locations within the gastrointestinal tract and/or at a certain pH within the gastrointestinal tract. The USP defines a modified release system as one in which the time course or location of drug release or both, are chosen to accomplish objectives of therapeutic effectiveness or convenience not fulfilled by immediate release dosage forms. A modified release oral dosage form can include extended release and delayed-release components. A delayed release dosage form is one that releases a drug all at once at a time other than promptly after administration. A modified release formulation can include delayed-release using enteric coatings, site-specific or timed release such as for colonic delivery, extended-release including, for example, formulations capable of providing zero-order, first-order, or biphasic release profiles, and programmed release such as pulsatile and delayed extended release.

"Sustained release" pharmaceutical compositions and coating provide for a dissolution rate over an extended period of time following oral administration. Granulations comprising granules having a sustained release coating can be referred to as sustained release granulations. A pharmaceutical composition comprising a sustained release granulation can be referred to as a sustained release pharmaceutical composition.

"pH-release" pharmaceutical compositions and coatings provide for an increased dissolution rate at an intended pH.

"Pulsatile release" pharmaceutical compositions and coatings exhibit an increased dissolution rate at intervals, where the release intervals can be determined by time, exposure to internal stimuli, or exposure to external stimuli. Examples of pulsatile-release systems include capsular systems, osmotic systems, systems having erodible membranes, and systems having a rupturable coating. Examples of stimuli include temperature, chemicals, electrical stimuli, and magnetic stimuli.

"Timed-release" pharmaceutical compositions and coatings have a dissolution rate that is a function of time. A time-release pharmaceutical composition or coating includes, for example, delayed release, sustained release, and extended release pharmaceutical compositions and coatings.

"Delayed release" pharmaceutical compositions and coatings provide for an increased dissolution rate at an intended time after administration.

"Modulate" and "modulation" refer to a change in biological activity for a biological molecule such as, for example, a protein, gene, peptide, or antibody, where such change may relate to an increase in biological activity such as, for example, increased activity, agonism, activation, expression, upregulation, and/or increased expression, or decrease in biological activity such as, for example, decreased activity, antagonism, suppression, deactivation, downregulation, and/or decreased expression, for the biological molecule. For example, compound (2) can modulate the p38α MAPK protein such as inhibit p38α MAPK protein. Compound (2) can selectively modulate such as selectively inhibit p38α MAPK protein as compared to other MAPK or p38 MAPK proteins. Compound (2) can selectively modulate such as selectively inhibit p38α MAPK protein as compared to other MAPK or p38 MAPK proteins.

"Moiety" refers to a specific segment or functional group of a molecule. Chemical moieties are often recognized chemical entities embedded within or appended to a molecule.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound provided by the present disclosure such as crystalline compound (1) or crystalline compound (2) and at least one pharmaceutically acceptable vehicle. A pharmaceutical composition can be administered to a patient. Pharmaceutically acceptable vehicles are known in the art.

"Disease" refers to a disease, disorder, condition, or symptom of any of the foregoing.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Curing" a disease refers to eliminating a disease or disorder or eliminating a symptom of a disease or disorder.

"Treating" or "treatment" of a disease or disorder refers to inhibiting the disease or disorder or one or more clinical symptoms of the disease or disorder, arresting the development of the disease or disorder or one or more clinical symptoms of the disease or disorder, relieving the disease or disorder or one or more clinical symptoms of the disease or disorder, causing the regression of the disease or disorder or one or more clinical symptoms of the disease or disorder, reducing the severity of one or more clinical symptom of the disease or disorder, delaying the onset of one or more clinical symptoms of the disease or disorder, mitigating one or more clinical symptoms of the disease or disorder and/or stabilizing the disease or disorder or one or more clinical symptoms of the disease or disorder. "Treating" or "treatment" of a disease or disorder includes producing a clinically beneficial effect without curing the underlying disease or disorder.

"Therapeutically effective amount" refers to the amount of a compound such as pharmaceutically active ingredient that, when administered to a patient for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, the severity of the disease and/or symptoms of the disease or disorder, the age, weight, and/or health of the patient to be treated, and the judgment of the prescribing physician. A therapeutically effective amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made to crystalline 4-chloro-N-(4-(morpholinomethyl)phenyl)benzamide and crystalline 4-chloro-N-(4-(morpholinomethyl)phenyl)benzamide hydrochloride, methods of making the crystalline compounds, pharmaceutical compositions comprising the crystalline compounds, and uses of the crystalline compounds. The crystalline compounds, pharmaceutical compositions, methods, and uses are not intended to be limiting of the claims. To the contrary, the claims are intended to cover all alternatives, modifications, and equivalents.

Crystalline compound (1), 4-chloro-N-(4-(morpholinomethyl)phenyl)benzamide hydrochloride, is a stable hydrochloride salt of 4-chloro-N-(4-(morpholinomethyl)phenyl)benzamide free base (Compound (2)).

Compound (1) has the structure:

(1)

Crystalline compound (1), crystalline 4-chloro-N-(4-(morpholinomethyl)phenyl)benzamide hydrochloride, is a stable salt of free base compound (2).

Crystalline compound (1) can be characterized by an XRPD (X-ray powder diffraction) pattern comprising characteristic diffraction peaks at least at 10.8±0.2°, 18.2°±0.2°, 14.8°±0.2°, 19.9±0.2°, 22.0±0.2°, 22.5±0.2°, 23.2±0.2°, 23.9±0.2°, 27.3±0.2°, 28.0±0.2°, and 29.2±0.2° expressed as 2θ angles and determined using Cu-Kα radiation.

Crystalline compound (1) can be characterized by an XRPD pattern comprising characteristic diffraction peaks at least at 10.8±0.1°, 18.2°±0.1°, 14.8°±0.1°, 19.9±0.1°, 22.0±0.1°, 22.5±0.1°, 23.2±0.1°, 23.9±0.1°, 27.3±0.1°, 28.0±0.2°, and 29.2±0.2° expressed as 2θ angles and determined using Cu-Kα radiation.

Figure 1:
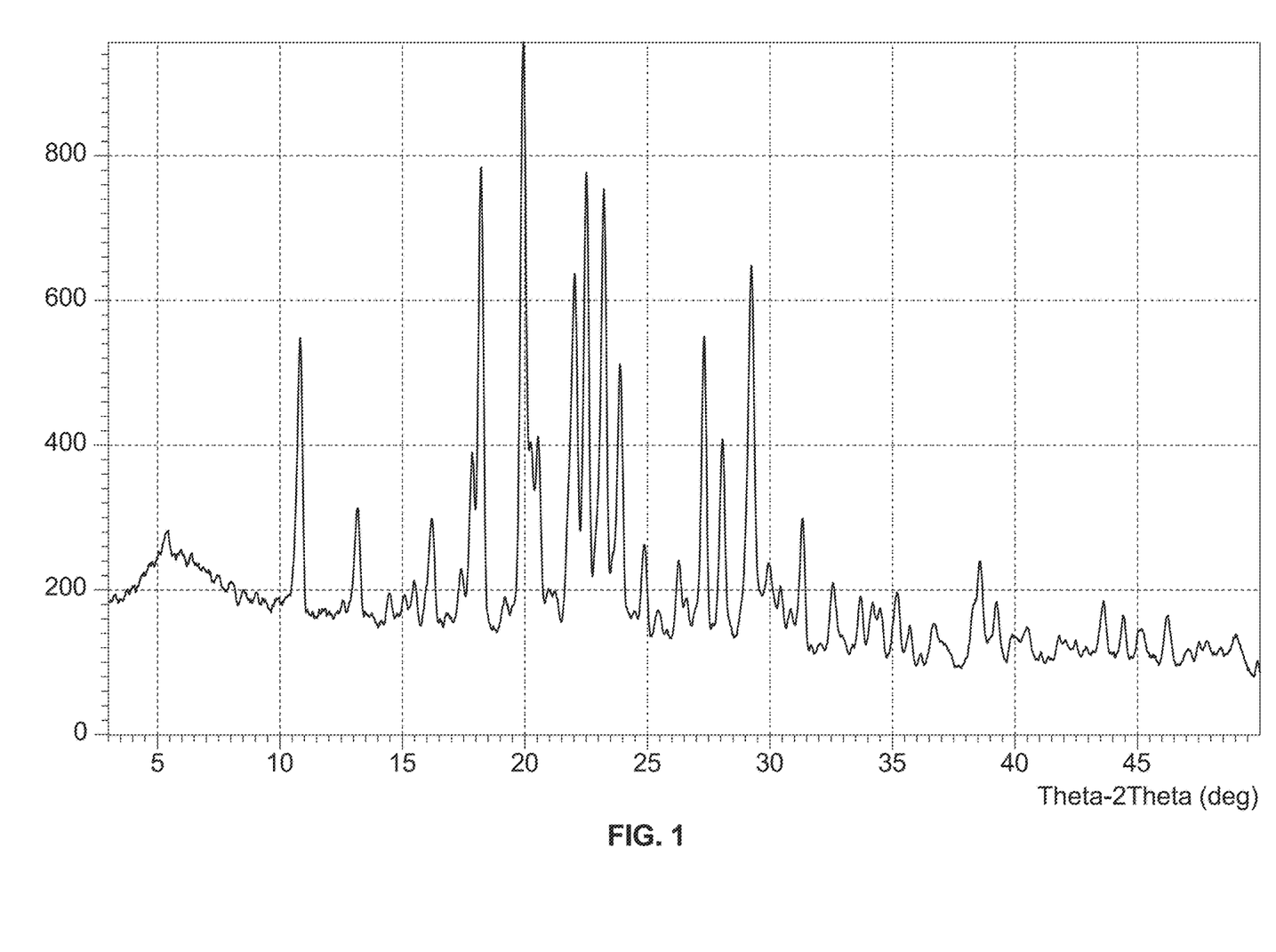
FIG. 1 shows an X-ray powder diffraction (XRPD) pattern of crystalline 4-chloro-N-(4-(morpholinomethyl)phenyl)benzamide hydrochloride.

Crystalline compound (1) can be characterized by an XRPD pattern as shown in FIG. 1.

Crystalline compound (1) can have an endothermic onset temperature, for example, from 220° C. to 230° C., such as from 222° C. to 228° C., or from 224° C. to 116° C., where the endothermic onset temperature is determined by differential scanning calorimetry.

Crystalline compound (1) can have an endothermic onset temperature, for example, of 225.6° C. 0.5° C., such as 225.5° C.±0.25° C., or 225.5° C.±0.1° C., where the endothermic onset temperature is determined by differential scanning calorimetry.

Crystalline compound (1) can have an endothermic enthalpy, for example, from 52 J/g to 62 J/g, from 54 J/g to 60 J/g, or from 56 J/g to 58 J/g, where the endothermic enthalpy is determined by differential scanning calorimetry.

Crystalline compound (1) can have an endothermic enthalpy, for example, of 57.2 J/g±0.5 J/g, such as 57.2 J/g±0.25 J/g, or 57.2 J/g±0.1 J/g, where the endothermic enthalpy is determined by differential scanning calorimetry.

Crystalline compound (1) can have an endothermic peak, for example, from 235° C. to 245° C., from 237° C. to 243° C., or from 239° C. to 241° C., where the endothermic peak is determined by differential scanning calorimetry.

Crystalline compound (1) can have an endothermic peak, for example, at 240° C.±2.0° C., such as 240° C.±1.0° C., or 240° C.±05° C., where the endothermic peak is determined by differential scanning calorimetry.

Figure 2:
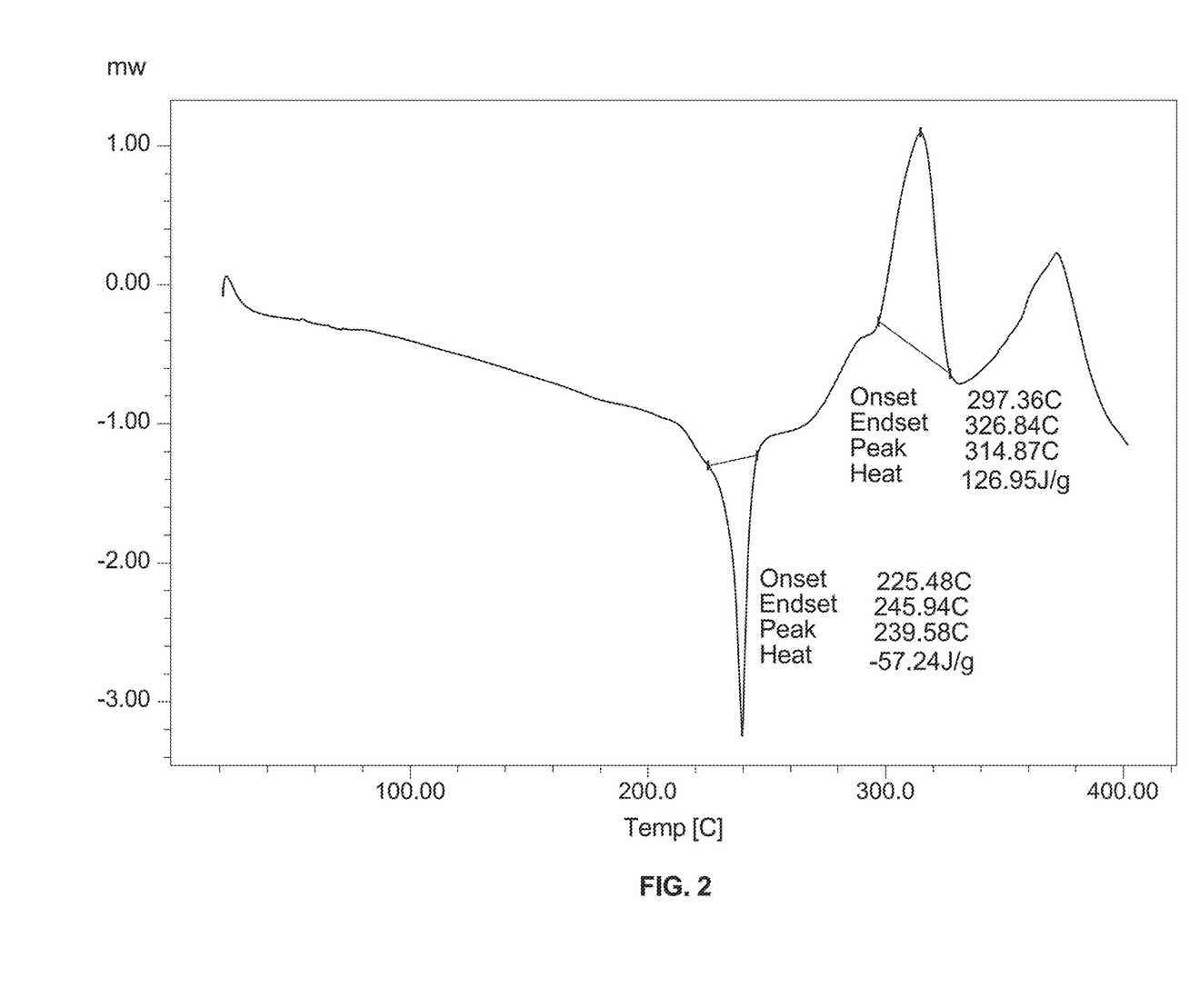
FIG. 2 shows a differential scanning calorimetry (DSC) scan of crystalline compound (1).

Crystalline compound (1) can exhibit a differential scanning calorimetry curve as shown in FIG. 2.

4-Chloro-N-(4-(morpholinomethyl)phenyl)benzamide is a substrate selective p38α MAPK inhibitor. 4-Chloro-N-(4-(morpholinomethyl)phenyl)benzamide (free base) has the structure of Formula (2):

(2)

Crystalline compound (2) can be characterized by an XRPD pattern comprising characteristic diffraction peaks at least at 19.9±0.2°, 20.9°±0.2°, 22.5°±0.2°, and 24.9±0.2° expressed as 2θ angles and determined using Cu-Kα radiation.

Crystalline compound (2) can be characterized by an XRPD pattern comprising characteristic diffraction peaks at least at 19.9±0.1°, 20.9°±0.1°, 22.5°±0.1°, and 24.9±0.1° expressed as 2θ angles and determined using Cu-Kα radiation.

Crystalline compound (2) can be characterized by an XRPD pattern comprising characteristic diffraction peaks at least at 17.1±0.2°, 18.0±0.2°, 19.9±0.2°, 20.9°±0.2°, 22.5°±0.2°, and 24.9±0.2°, 27.0±0.2°, and 31.1±0.2° expressed as 2θ angles and determined using Cu-Kα radiation.

Crystalline compound (2) can be characterized by an XRPD pattern comprising characteristic diffraction peaks at least at 17.1±0.1°, 18.0±0.1°, 19.9±0.2°, 20.9°±0.1°, 22.5°±0.1°, and 24.9±0.1°, 27.0±0.1°, and 31.1±0.1° expressed as 2θ angles and determined using Cu-Kα radiation.

Figure 3:
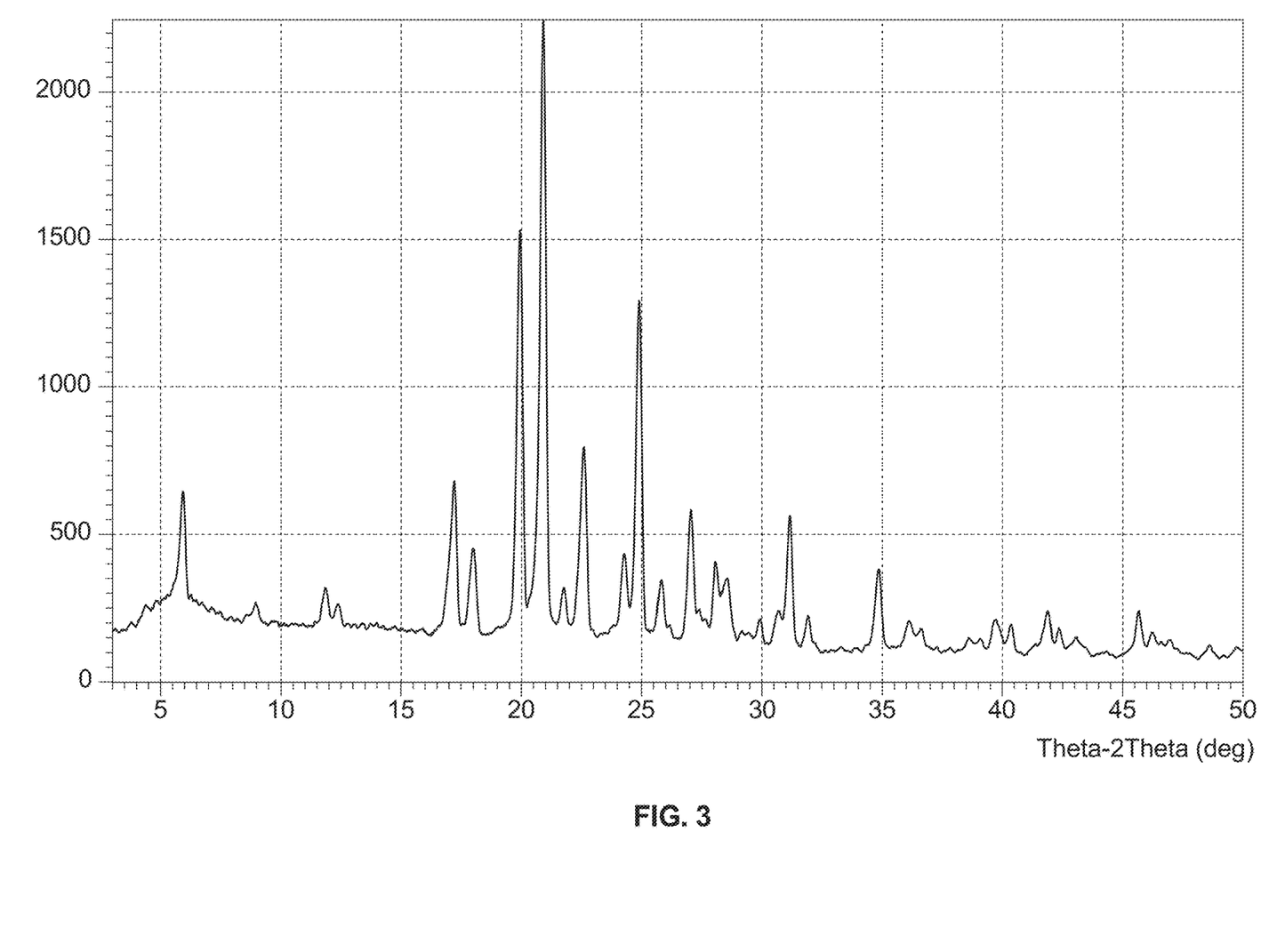
FIG. 3 shows an X-ray powder diffraction (XRPD) pattern of crystalline 4-chloro-N-(4-(morpholinomethyl)phenyl)benzamide.

Crystalline compound (2) can be characterized by an XRPD pattern as shown in FIG. 3.

A method of synthesizing Compound (1) is provided in Example 1. 4-Chloro-N-(4-(morpholinomethyl)phenyl)benzamide hydrochloride can be synthesized by reacting 4-chloro-N-(4-(morpholinomethyl)phenyl)benzamide with hydrochloric acid in an inert solvent. For example, the inert solvent can comprise tetrahydrofuran and 1,4-dioxane. The reaction can be undertaken, for example, at a temperature from 0° C. to 5° C. The compound can be crystallized to provide crystalline compound (1).

A method of synthesizing compound (2) is provided in Example 2.

A method of synthesizing 4-chloro-N-(4-(morpholinomethyl)phenyl)benzamide can comprise: reacting 4-amino benzyl alcohol with 4-chlorobenzoyl chloride to provide 4-chloro-N-(4-(hydroxymethyl)phenyl)benzamide; reacting 4-chloro-N-(4-(hydroxymethyl)phenyl)benzamide with thionyl chloride to provide 4-chloro-N-(4-(chloromethyl)phenyl)benzamide; and reacting 4-chloro-N-(4-(chloromethyl)phenyl)benzamide with morpholine to provide 4-chloro-N-(4-(morpholinomethyl)phenyl)benzamide.

Reacting 4-amino benzyl alcohol with 4-chlorobenzoyl chloride to provide 4-chloro-N-(4-(hydroxymethyl)phenyl)

benzamide can comprise reacting in ethyl acetate in the presence of potassium carbonate at a temperature of from 0° C. to 5° C.

Reacting 4-chloro-N-(4-(hydroxymethyl)phenyl)benzamide with thionyl chloride to provide 4-chloro-N-(4-(chloromethyl)phenyl)benzamide can comprise reacting in dichloromethane at a temperature from 0° C. to 5° C.

Reacting 4-chloro-N-(4-(chloromethyl)phenyl)benzamide with morpholine to provide 4-chloro-N-(4-(morpholinomethyl)phenyl)benzamide in dichloromethane can comprise reacting at a temperature from 0° C. to 5° C.

4-Chloro-N-(4-(morpholinomethyl)phenyl)benzamide can be crystallized to provide crystalline 4-chloro-N-(4-(chloromethyl)phenyl)benzamide.

A pharmaceutical composition provided by the present disclosure can comprise crystalline compound (1) or crystalline compound (2).

A pharmaceutical composition can comprise a therapeutically effective amount of crystalline compound (1) or crystalline compound (2) for treating a disease in a patient.

A pharmaceutical composition can comprise one or more pharmaceutically acceptable carriers, excipients diluents, or combinations of any of the foregoing.

A crystalline compound can be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. Pharmaceutical compositions provided by the present disclosure can be injectable intravenous formulations. Pharmaceutical compositions provided by the present disclosure can be oral formulations. Oral formulations may be oral dosage forms. A pharmaceutical composition may be formulated for intravenous administration or for subcutaneous administration.

Pharmaceutical compositions provided by the present disclosure may comprise a therapeutically effective amount of a crystalline compound together with a suitable amount of one or more pharmaceutically acceptable vehicles so as to provide a composition for proper administration to a patient. Suitable pharmaceutical vehicles and methods of preparing pharmaceutical compositions are described in the art.

A pharmaceutical composition provided by the present disclosure can be formulated for oral administration. A pharmaceutical composition formulated for oral administration can comprise any suitable oral dosage form including, for example, tablets, capsules, caplets, sachets, bottles, stick packs, dispersions, and suspensions.

A pharmaceutical composition formulated for oral administration can provide for a modified release profile in the gastrointestinal tract, such as a controlled release profile, a sustained release profile, a pH-release profile, a pulsatile release profile, a timed-release profile, or a delayed release profile. A pharmaceutical composition formulated for oral administration can be configured to release a crystalline compound over an intended period of time following ingestion and/or in an intended region of the gastrointestinal tract.

A pharmaceutical composition formulated for oral administration can provide for an immediate release profile.

Assessing single patient response to therapy and qualifying a patient for optimal therapy are among the greatest challenges of modern healthcare and relate to trends in personalized medicine. Compound (1) can have target selectivity, for example, for certain cancers and immune cells. A crystalline compound radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using a crystalline compound, once correlated to the concentration can provide a three-dimensional distribution map, which can then be used for macroscopic dose calculations.

Accordingly, it is within the capability of those of skill in the art to assay and use a crystalline compound and/or pharmaceutical compositions thereof for therapy.

Compound (1) and/or pharmaceutical composition thereof can generally be used in an amount effective to achieve the intended purpose. For use to treat a disease such as cancer, an autoimmune disease a respiratory disease, an age-related disease, or an inflammatory disease, a crystalline compound can be administered or applied in a therapeutically effective amount.

The amount of a crystalline compound) that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a crystalline compound can depend on, among other factors, the patient being treated, the weight of the patient, the severity of the affliction, the manner of administration and the judgment of the prescribing physician.

A crystalline compound can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

A therapeutically effective dose of a crystalline compound and/or pharmaceutical composition thereof will provide therapeutic benefit without causing substantial toxicity. Toxicity of a crystalline compound and/or pharmaceutical composition thereof may be determined using standard pharmaceutical procedures and may be readily ascertained by the skilled artisan. The dose ratio between toxic and therapeutic effect is the therapeutic index. A crystalline compound and/or pharmaceutical composition thereof exhibits a particularly high therapeutic index in treating disease and disorders. A dose of a crystalline compound and/or pharmaceutical composition thereof can be within a range of circulating concentrations that include an effective dose with minimal toxicity.

Crystalline compound (1) or crystalline compound (2) or a pharmaceutical composition thereof may be included in a kit that may be used to administer the compound to a patient for therapeutic purposes. A kit can include a pharmaceutical composition comprising a crystalline compound suitable for administration to a patient and instructions for administering the pharmaceutical composition to the patient. A kit can be suitable for treating cancer, for treating an autoimmune disease, for treating an age-related disease, for treating a respiratory disease, or for treating an inflammatory disease. A kit can comprise a crystalline compound, a pharmaceutically acceptable vehicle for administering the cocrystal, and instructions for administering the formulation comprising the cocrystal to a patient.

The pharmaceutical compositions can be included, for example, in a container, packet, sachet, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Crystalline compound (1) and crystalline compound (2) and pharmaceutical compositions comprising a crystalline compound can be used to treat a disease in which the etiology of the disease is associated with p38α MAPK protein activity.

Compound (2) is a selective inhibitor of p38α MAPK. A selective p38α MAPK inhibitor has a higher binding affinity to the target pocket of p38α MAPK than to the catalytic binding site of p38α MAPK. A p38α MAPK inhibitor can bind to p38α MAPK near the substrate binding groove of p38α MAPK, which extends between two acidic regions, the CD and ED domains. The binding pocket can be defined at least by residues R49, H107, L108, and K165 of p38α MAPK. The binding pocket can be defined at least by residues R49, H107, L108, M109, G1 10, A1 57, V158, E1 63, L164, and K165 of p38α MAPK.

Selective binding of compound (2) p38α MAPK can be confirmed using complementary technologies. For example, a selective p38α MAPK inhibitor can show a concentration-dependent increase in melting temperature of p38α but not p38β as determined using DSF, which detects ligand-induced protein stabilization. STD-NMR, which measures low affinity protein/ligand binding via non-scalar magnetization transfer from protein to ligand protons, can be used to confirm specific compound binding to p38α and localized the interaction to its aromatic rings. A p38α MAPK inhibitor can cause a concentration-dependent increase in melting temperature of p38α MAPK. The difference in melting temperature $T_m$ can be measured at a p38α MAPK inhibitor concentration of between 1 nM and 1000 μM such as at a concentration of 100 μM. For example, the difference in the melting temperature can be from 0.1° C. and about 2° C.

Compound (2) can interact with a pocket near the ED substrate docking site of p38 MAPK.

Compound (2) can bind to p38α MAPK near the substrate binding groove of p38α MAPK, which extends between the CD and ED domains.

Compound (2) can inhibit MK2 phosphorylation through interaction with p38α MAPK.

Compound (2) can competitively bind to p38α MAPK with 4-chloro-N-(4-((1,1-dioxidothiomorpholino)methyl)phenyl)benzamide.

Compound (2) can have a higher binding affinity to the p38α MAPK subunit than to the p38β MAPK subunit.

Phosphorylation of MK2 requires binding to the ED site adjacent to the target pocket in p38α MAPK. The target pocket can be defined by amino acids R49, H107, L108, and K165 in p38α MAPK. The target pocket can be defined by amino acids selected from R49, H107, L108, M109, G1 10, A1 57, V158, E1 63, L164, and K165 in p38α MAPK. The target pocket can be defined by the amino acids R49, H107, L108, M109, G1 10, A1 57, V158, E1 63, L164, and K165 in p38α MAPK.

Compound (2) can at least partially inhibit MK2 phosphorylation. For example, Western blotting can be used to measure inhibition of MK2 phosphorylation in anisomycin-stimulated HeLa cells by compound (2).

Compound (2) can stabilize an endothelial or epithelial barrier function. Endothelial barrier permeability can be measured by separate or combined exposure to TNFα and hyperthermia, followed by measurement of permeably for 10 kDa dextran. For example, endothelial barrier stabilization can be assessed by pretreating with compound (2), preceded and followed by permeability measurements, where stabilization can be expressed as a percent reduction in the before and after pretreatment permeability increase. A permeability increase for 10 kDa dextran can be reduced by between 5% to more than 100% such as, for example, by greater than 5%, greater than 10%, greater than 20%, greeter than 40%, greater than 60%, greater than 80%, or greater than 100%.

Compound (2) can modulate TNFa-induced gene expression in human lung microvascular endothelial cells (HMVECLs) as determined using, for example, RNASeq. For example, HMVECLs can be pretreated for a period of time with a p38α MAPK inhibitor at an appropriate concentration and then stimulated with TNFa for a period of time. Compound (1) can inhibit genes such as PRRG4, TSLP, CCLI 7, EXOC3L4, MMP9, IDOI, CXCL1O, CD200, SLCI5A3, VDR, ILIB, GPR88, CD207, TCHH, HAS3, GBPIPI, MUC4, ELOVL7, CXCL11, GBP4, PLAIA, and/or CXCL5.

The effects of a p38α MAPK inhibitor on inflammatory cytokine expression can be determined by pretreating PMA-differentiated THPI cells with a p38α MAPK inhibitor, then stimulating with LPS, and harvesting RNA a period of time later for analysis by PCR-based cytokine array. A p38α MAPK inhibitor can inhibit expression of various genes, such as IL-IA, IL-8, TNFSF8, CXCL5, CCL7, CCLI7, TNFSF9, IL-IB, CXCLI, TNFSFI5, CCL5, CCL4, CCL20, CXCL2, TNF, or BMP6. A p38α MAPK inhibitor can inhibit expression of Smad3, which drives differentiation of Foxp3 T regulatory cells and suppresses interferon-γ. Inflammation reduction can be measured by comparing the fold change mRNA levels vs. unstimulated PMA-differentiated THPI cells at various concentrations of p38α MAPK inhibitor.

Crystalline compound (1) or crystalline compound (2) or a pharmaceutical composition thereof can be used to treat a disease in a patient.

A crystalline compound or a pharmaceutical composition thereof can be used to treat a disease in which the etiology of the disease is associated with up-regulation and/or down-regulation of the p38α MAPK protein.

Methods provided by the present disclosure include treating a disease in a patient comprising administering to a patient in need of such treatment a therapeutically effective amount of a crystalline compound or a pharmaceutical composition thereof, wherein the disease is treated by inhibiting the p38α MAPK protein.

The p38 mitogen-activated protein kinase (MAPK) family of stress- and cytokine-activated kinases are associated with the pathogenesis of many human diseases, including, for example, cancer, rheumatoid arthritis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by p38 MAPK, regulation of endothelial and epithelial barrier function, leukocyte trafficking, and cytokine expression are central to the pathogenesis of acute and chronic inflammatory disorders.

Crystalline compound (1) or crystalline compound (2) or a pharmaceutical composition thereof can be used for treating cancer in a patient. The cancer can be, for example, a solid tumor or a metastasis.

Methods provided by the present disclosure include methods of treating cancer in a patient comprising administering to a patient in need of such treatment a therapeutically effective amount of a compound or pharmaceutical composition provided by the present disclosure.

Examples of suitable cancers include acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, Examples of suitable cancers include pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma, and the like. In other embodiments, the cancer is acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendothelioma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom macroglobulinemia.

Crystalline compound (1) or crystalline compound (2) or a pharmaceutical composition thereof can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

Methods provided by the present disclosure include methods of treating cancer, where the cancer is selected from breast cancer and melanoma.

Methods provided by the present disclosure include methods of treating an inflammatory disease in a patient comprising administering to a patient in need of such treatment a therapeutically effective amount of a compound or pharmaceutical composition provided by the present disclosure.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Methods provided by the present disclosure include methods of treating an inflammatory disease in a patient, where the inflammatory disease is selected from, for example, acute respiratory distress syndrome, focal segmental glomerulonephrits, atherosclerosis/acute coronary syndrome, chronic obstructive pulmonary disease, asthma, inflammatory bowel disease, Crohn's disease, psoriasis, lupus, multiple sclerosis, inflammation in hypoercholesteremia, pain, diabetes, and rheumatoid arthritis.

Methods provided by the present disclosure include methods of treating an autoimmune disease in a patient comprising administering to a patient in need of such treatment a therapeutically effective amount of a compound or pharmaceutical composition provided by the present disclosure.

A crystalline compound or a pharmaceutical composition thereof can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases*, Rose and Mackay, 2014, Academic Press.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Behcet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxcackie myocarditits, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Gullain-Barre syndrome, Hashimoto's thyroiditis, hemolytic anemia, Henoch-Schonlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonnage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vaculitis, vitiligo, and Wegener's granulomatosis.

Crystalline compound (1) or crystalline compound (2) or a pharmaceutical composition thereof can be used to treat autoimmune disorders such as, for example, lupus, graft-versus-host disease, hepatitis C-induced vasculitis, Type I diabetes, multiple sclerosis, spontaneous loss of pregnancy, atopic diseases, and inflammatory bowel diseases.

Crystalline compound (1) or crystalline compound (2) or a pharmaceutical composition thereof can be administered with one or more additional therapeutic agents for treating an autoimmune disease. Compound (1) or a pharmaceutical composition thereof may be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

Methods provided by the present disclosure include methods of treating a disease in a patient comprising administering to a patient in need of such treatment a therapeutically effective amount of crystalline compound (1) or crystalline compound (2), wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis. Crystalline compound (1) or crystalline compound (2) or a pharmaceutical composition thereof can be administered to a patient to treat a symptom of a viral infection such as a COVID19 infection.

Methods provided by the present disclosure include methods of treating a disease in a patient comprising administering to a patient in need of such treatment a therapeutically effective amount of crystalline compound (1) or crystalline compound (2), wherein the disease is a respiratory disease.

Methods provided by the present disclosure include methods of treating a disease in a patient comprising administering to a patient in need of such treatment a therapeutically effective amount of crystalline compound (1) or crystalline compound (2) or pharmaceutical composition provided by the present disclosure, wherein the disease is an age-related disease such as, for example, hearing loss, muscle degeneration, Werner's syndrome, cellular aging, or Alzheimer's disease.

Methods provided by the present disclosure include methods of treating a disease in a patient comprising administering to a patient in need of such treatment a therapeutically effective amount of a crystalline compound or a pharmaceutical composition of such treatment, wherein the disease is selected from sudden idiopathic hearing loss, drug induced hearing loss, age-related hearing loss, and Duchenne muscular dystrophy.

The amount of crystalline compound (1) or crystalline compound (2), or pharmaceutical composition thereof that will be effective in the treatment of a cancer can depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a crystalline compound) administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a crystalline compound (1) or crystalline compound (2) and appropriate dosing intervals may be selected to maintain a sustained therapeutically effective concentration of compound (2) in the blood of a patient, and in certain embodiments, without exceeding a minimum adverse concentration.

A pharmaceutical composition comprising crystalline compound (1) or crystalline compound (2) may be administered, for example, 4 time per day, twice a day, once a day, once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of a crystalline compound contained within each of the multiple dosage forms may be the same or different.

Suitable daily dosage ranges for administration can range, for example, from about 2 µg to about 200 mg of a crystalline compound per kilogram body weight.

Suitable daily dosage ranges for administration may range, for example, from about 1 µg to about 50 mg of crystalline compound (1) or crystalline compound (2) per square meter ($m^2$) of body surface.

A crystalline compound may be administered to treat cancer in a patient in an amount, for example, from 0.001 mg/day to 100 mg/day, or in any other appropriate daily dose. A dose can be, for example, from 0.01 µg/kg body weight/week to 100 µg/kg body weight/week or any other suitable dose.

A pharmaceutical composition comprising crystalline compound (1) or crystalline compound (2) may be administered to treat cancer in a patient so as to provide a therapeutically effective concentration of compound (2) in the blood or plasma of the patient. A therapeutically effective concentration of compound (2) in the blood of a patient can be, for example, from 0.01 µg/L to 1,000 µg/L, from 0.1 µg/L to 500 µg/L, from 1 µg/L to 250 µg/L, or from about 10 µg/L to about 100 µg/L. A therapeutically effective concentration of compound (2) in the blood of a patient can be, for example, at least 0.01 µg/L, at least 0.1 µg/L, at least 1 µg/L, at least about 10 µg/L, or at least 100 µg/L. A therapeutically effective concentration of compound (2) in the blood of a patient can be, for example, less than an amount that causes unacceptable adverse effects including adverse effects to homeostasis. A therapeutically effective concentration of compound (2) in the blood of a patient can be an amount sufficient to restore and/or maintain homeostasis in the patient.

Pharmaceutical compositions provided by the present disclosure may be administered to treat a disease in a patient so as to provide a therapeutically effective concentration of compound (2) in the blood of a patient for a period of time such as, for example, for 4 hours, 8 hours, 12 hours, 16 hours, 20 hours, 1 day, or 2 days.

The amount of a crystalline compound administered may vary during a treatment regimen.

Pharmaceutical compositions provided by the present disclosure may further comprise one or more pharmaceutically active compounds in addition to a crystalline compound. Such compounds may be provided, for example, to treat the disease being treated with crystalline compound (1) or crystalline compound (2) or to treat a disease, disorder, or condition other than the disease being treated with crystalline compound (1) or crystalline compound (2), to treat a side-effect caused by compound (2), to augment the efficacy of compound (2), and/or to modulate the activity of compound (2).

A crystalline compound may be administered in combination with at least one other therapeutic agent. A crystalline compound may be administered to a patient together with another compound for treating the disease in the patient. A crystalline compound and the at least one other therapeutic agent may act additively or, and in certain embodiments, synergistically. The at least one additional therapeutic agent may be included in the same pharmaceutical composition or vehicle comprising a crystalline compound or may be in a separate pharmaceutical composition or vehicle. Accordingly, methods provided by the present disclosure further include, in addition to administering a crystalline compound, administering one or more therapeutic agents effective for treating cancer or a different disease, disorder or condition than cancer. Methods provided by the present disclosure include administering a crystalline compound and one or more other therapeutic agents provided that the combined administration does not inhibit the therapeutic efficacy of compound (2) and/or does not produce adverse combination effects.

A pharmaceutical composition comprising crystalline compound (1) or crystalline compound (2) may be administered concurrently with the administration of another therapeutic agent, which may be part of the same pharmaceutical composition as, or in a different pharmaceutical composition than that comprising a crystalline compound. A crystalline compound may be administered prior or subsequent to administration of another therapeutic agent. In certain combination therapies, the combination therapy may comprise alternating between administering a crystalline compound) and a composition comprising another therapeutic agent, e.g., to minimize adverse drug effects associated with a particular drug. When a crystalline compound is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising crystalline compound (1) or crystalline compound (2) may be administered with one or more substances, for example, to enhance, modulate and/or control release, bioavailability, therapeutic efficacy, therapeutic potency, and/or stability, of a crystalline compound. For example, a pharmaceutical composition comprising a crystalline compound can be co-administered with an active agent having pharmacological effects that enhance the therapeutic efficacy of compound (2).

Crystalline compound (1) or crystalline compound (2) or a pharmaceutical composition thereof may be administered in conjunction with an agent known or believed to be effective in treating a disease such as cancer, an autoimmune disease, an inflammatory disease, or an age-related disease in a patient, such as the same disease being treated with a crystalline compound.

The efficacy of administering a crystalline compound or a pharmaceutical composition thereof for treating cancer, an inflammatory disease, an autoimmune disease, or an age-related disease may be assessed using in vitro and animal studies and in clinical trials.

Methods of inhibiting p38α MAPK provided by the present disclosure include contacting p38α MAPK with a compound provided by the present disclosure to a pocket near the ED substrate-docking site of p38α MAPK.

Methods of inhibiting p38α MAPK provided by the present disclosure do not result in loss of p38α-dependent counterregulatory responses. The p38α-dependent counterregulatory response relates to mitogen- and stress-activated protein kinase-I (MSK1), or MSK2. In targeting a pocket near the ED substrate-docking site of p38α, the inhibitors provided by the present disclosure avoid interfering with CD-specific substrates, including MSK1/2, thus limiting inflammation through expression of IL-10 and DUSP2.

ASPECTS OF THE INVENTION

The invention is further defined by the following aspects.

Aspect 1. A compound, crystalline 4-chloro-N-(4-(morpholinomethyl)phenyl)benzamide hydrochloride:

Aspect 2. The compound of aspect 1, wherein the compound is characterized by an XRPD pattern comprising characteristic diffraction peaks at least at 10.8±0.2°, 18.2°±0.2°, 14.8°±0.2°, 19.9±0.2°, 22.0±0.2°, 22.5±0.2°, 23.2±0.2°, 23.9±0.2°, 27.3±0.2°, 28.0±0.2°, and 29.2±0.2° expressed as 2θ angles and determined using Cu-Kα radiation.

Aspect 3. The compound of aspect 1, wherein the compound is characterized by an XRPD pattern comprising characteristic diffraction peaks at least at 10.8±0.1°, 18.2°±0.1°, 14.8°±0.1°, 19.9±0.1°, 22.0±0.1°, 22.5±0.1°, 23.2±0.1°, 23.9±0.1°, 27.3±0.1°, 28.0±0.2°, and 29.2±0.2° expressed as 2θ angles and determined using Cu-Kα radiation.

Aspect 4. The compound of aspect 1, wherein the compound is characterized by an XRPD pattern as shown in FIG. 1.

Aspect 5. The compound of any one of aspects 1 to 4, wherein the compound has an endothermic onset temperature from 220° C. to 230° C., where the endothermic onset temperature is determined by differential scanning calorimetry.

Aspect 6. The compound of any one of aspects 1 to 5, wherein the compound has an endothermic peak from 235° C. to 245° C., where the endothermic peak is determined by differential scanning calorimetry.

Aspect 7. The compound of any one of aspects 1 to 6, wherein the compound has an endothermic enthalpy from 52 J/g to 62 J/g, where the endothermic enthalpy is determined by differential scanning calorimetry.

Aspect 8. The compound of any one of aspects 1 to 7, wherein the compound has an exothermic onset temperature from 292° C. to 302° C., where the exothermic onset temperature is determined by differential scanning calorimetry.

Aspect 9. The compound of any one of aspects 1 to 8, wherein the compound has an exothermic peak from 310° C. to 320° C., where the exothermic peak is determined by differential scanning calorimetry.

Aspect 10. The compound of any one of aspects 1 to 9, wherein the compound has an exothermic enthalpy from 122

J/g to 132 J/g, where the exothermic enthalpy is determined by differential scanning calorimetry.

Aspect 11. The compound of any one of aspects 1 to 10, wherein the compound exhibits a differential scanning calorimetry curve as shown in FIG. 2.

Aspect 12. A pharmaceutical composition comprising the compound of any one of aspects 1 to 11 and a pharmaceutically acceptable excipient.

Aspect 13. The pharmaceutical composition of aspect 12, wherein the pharmaceutical composition comprises a therapeutically effective amount of the compound for treating a disease in a patient, wherein the disease is selected from cancer, an inflammatory disease, a respiratory disease, an age-related disease, and an autoimmune disease.

Aspect 14. The pharmaceutical composition of aspect 13, wherein the disease is an inflammatory disease.

Aspect 15. The pharmaceutical composition of aspect 14, wherein the inflammatory disease is selected from acute lung injury, acute respiratory distress syndrome (ARDS), and chronic obstructive pulmonary disease (COPD).

Aspect 16. A method of treating a disease in a patient comprising administering to a patient in need of such treatment a therapeutically effective of amount of the compound of any one of aspects 1 to 11, wherein the disease is selected from cancer, an inflammatory disease, an autoimmune disease, a respiratory disease, and an age-related disease.

Aspect 17. The method of aspect 16, wherein the disease is cancer.

Aspect 18. The method of aspect 17, wherein the cancer is selected from breast cancer and melanoma.

Aspect 19. The method of aspect 16, wherein the disease is an inflammatory disease.

Aspect 20. The method of aspect 19, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Aspect 21. The method of aspect 16, wherein the disease is an autoimmune disease.

Aspect 22. The method of aspect 16, wherein the disease is an age-related disease.

Aspect 23. The method of aspect 22, wherein the age-related disease is selected from hearing loss, muscle degeneration, Werner's syndrome, cellular aging, and Alzheimer's disease.

Aspect 24. A method of treating a disease in a patient comprising administering to a patient in need of such treatment a therapeutically effective of amount of the compound of any one of aspects 1 to 11, wherein the disease is selected from acute lung injury, acute respiratory distress syndrome (ARDS), and chronic obstructive pulmonary disease (COPD).

Aspect 25. A method of making 4-chloro-N-(4-(morpholinomethyl)phenyl)benzamide hydrochloride comprising reacting 4-chloro-N-(4-(morpholinomethyl)phenyl)benzamide with hydrochloric acid.

Aspect 26. The method of aspect 25, wherein reacting comprises reacting in a solvent comprising tetrahydrofuran and 1,4-dioxane.

Aspect 27. The compound 4-chloro-N-(4-(morpholinomethyl)phenyl)benzamide hydrochloride made by the method of any one of aspects 25 and 26.

Aspect 28. A compound, crystalline 4-chloro-N-(4-(morpholinomethyl)phenyl)benzamide:

Aspect 29. The compound of aspect 28, wherein the compound is characterized by an XRPD pattern comprising characteristic diffraction peaks at least at 19.9±0.2°, 20.9°±0.2°, 22.5°±0.2°, and 24.9±0.2° expressed as 2θ angles and determined using Cu-Kα radiation.

Aspect 30. The compound of aspect 28, wherein the compound is characterized by an XRPD pattern comprising characteristic diffraction peaks at least at 19.9±0.1°, 20.9°±0.1°, 22.5°±0.1°, and 24.9±0.1° expressed as 2θ angles and determined using Cu-Kα radiation.

Aspect 31. The compound of aspect 28, wherein the compound is characterized by an XRPD pattern comprising characteristic diffraction peaks at least at 17.1±0.2°, 18.0±0.2°, 19.9±0.2°, 20.9°±0.2°, 22.5°±0.2°, and 24.9±0.2°, 27.0±0.2°, and 31.1±0.2° expressed as 2θ angles and determined using Cu-Kα radiation.

Aspect 32. The compound of aspect 28, wherein the compound is characterized by an XRPD pattern comprising characteristic diffraction peaks at least at 17.1±0.1°, 18.0±0.1°, 19.9±0.2°, 20.9°±0.1°, 22.5°±0.1°, and 24.9±0.1°, 27.0±0.1°, and 31.1±0.1° expressed as 2θ angles and determined using Cu-Kα radiation.

Aspect 33. The compound of aspect 28, wherein the compound is characterized by an XRPD pattern as shown in FIG. 3.

Aspect 34. A pharmaceutical composition comprising the compound of any one of aspects 28 to 33 and a pharmaceutically acceptable excipient.

Aspect 35. The pharmaceutical composition of aspect 34, wherein the pharmaceutical composition comprises a therapeutically effective amount of the compound for treating a disease in a patient, wherein the disease is selected from cancer, an inflammatory disease, a respiratory disease, an age-related disease, and an autoimmune disease.

Aspect 36. The pharmaceutical composition of aspect 35, wherein the disease is an inflammatory disease.

Aspect 37. The pharmaceutical composition of aspect 36, wherein the inflammatory disease is selected from acute lung injury, acute respiratory distress syndrome (ARDS), and chronic obstructive pulmonary disease (COPD).

Aspect 38. A method of treating a disease in a patient comprising administering to a patient in need of such treatment a therapeutically effective of amount of the compound of any one of aspects 28 to 33, wherein the disease is selected from cancer, an inflammatory disease, an autoimmune disease, a respiratory disease, and an age-related disease.

Aspect 39. The method of aspect 38, wherein the disease is cancer.

Aspect 40. The method of aspect 39, wherein the cancer is selected from breast cancer and melanoma.

Aspect 41. The method of aspect 38, wherein the disease is an inflammatory disease.

Aspect 42. The method of aspect 41, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Aspect 43. The method of aspect 38, wherein the disease is an autoimmune disease.

Aspect 44. The method of aspect 38, wherein the disease is an age-related disease.

Aspect 45. The method of aspect 44, wherein the age-related disease is selected from hearing loss, muscle degeneration, Werner's syndrome, cellular aging, and Alzheimer's disease.

Aspect 46. A method of treating a disease in a patient comprising administering to a patient in need of such treatment a therapeutically effective of amount of the compound of any one of aspects 28 to 33, wherein the disease is selected from acute lung injury, acute respiratory distress syndrome (ARDS), and chronic obstructive pulmonary disease (COPD).

Aspect 47. A method of making 4-chloro-N-(4-(morpholinomethyl)phenyl)benzamide comprising: reacting 4-amino benzyl alcohol with 4-chlorobenzoyl chloride to provide 4-chloro-N-(4-(hydroxymethyl)phenyl)benzamide; reacting 4-chloro-N-(4-(hydroxymethyl)phenyl)benzamide with thionyl chloride to provide 4-chloro-N-(4-(chloromethyl)phenyl)benzamide; and reacting 4-chloro-N-(4-(chloromethyl)phenyl)benzamide with morpholine to provide 4-chloro-N-(4-(morpholinomethyl)phenyl)benzamide.

Aspect 48. The method of aspect 47, wherein reacting 4-amino benzyl alcohol with 4-chlorobenzoyl chloride to provide 4-chloro-N-(4-(hydroxymethyl)phenyl)benzamide comprises reacting in ethyl acetate in the presence of potassium carbonate at a temperature of from 0° C. to 5° C.

Aspect 49. The method of any one of aspects 47 and 48, wherein reacting 4-chloro-N-(4-(hydroxymethyl)phenyl)benzamide with thionyl chloride to provide 4-chloro-N-(4-(chloromethyl)phenyl)benzamide comprises reacting in dichloromethane at a temperature from 0° C. to 5° C.

Aspect 50. The method of any one of aspects 47 to 49, wherein reacting 4-chloro-N-(4-(chloromethyl)phenyl)benzamide with morpholine to provide 4-chloro-N-(4-(morpholinomethyl)phenyl)benzamide in dichloromethane at a temperature from 0° C. to 5° C.

Aspect 51. The compound 4-chloro-N-(4-(morpholinomethyl)phenyl)benzamide made by the method of any one of aspects 47 to 49.

Aspect 52. A method of treating a disease in a patient comprising administering to a patient in need of such treatment a therapeutically effective of amount of the compound of any one of aspects 1 to 11 and 28 to 33, wherein the disease is treated by inhibiting the p38α MAPK receptor.

Aspect 53. A method of inhibiting the p38α MAPK receptor comprising contacting the p38α MAPK receptor with the compound of any one of aspects 1 to 11 and 28 to 33.

Aspect 54. A method of inhibiting the p38α MAPK receptor in a patient comprising administering to a patient a pharmacologically effective amount of the compound of any one of aspects 1 to 11 and 28 to 33.

Aspect 55. The method of aspect 54, wherein inhibiting the p38α MAPK receptor comprises selectively inhibiting the p38α MAPK receptor.

Aspect 56. The method of aspect 55, wherein inhibiting the p38α MAPK receptor does not result in loss of a p38α-dependent counterregulatory response.

Aspect 57. The method of aspect 56, wherein the p38α-dependent counterregulatory response relates to mitogen- and stress-activated protein kinase-1 (MSK1) or MSK2.

Aspect 58. The method of aspect 54, wherein inhibiting the p38α MAPK receptor stabilizes an endothelial or epithelial barrier function.

Aspect 59. The method of aspect 54, wherein inhibiting the p38α MAPK receptor reduces inflammation.

Aspect 60. The method of aspect 54, wherein inhibiting the p38α MAPK receptor mitigates KPS-induced lung injury.

Aspect 61. The method of aspect 54, wherein inhibiting the p38α MAPK receptor regulates leukocyte trafficking.

Aspect 62. The method of aspect 54, wherein inhibiting the p38α MAPK receptor regulates cytokine expression.

EXAMPLES

The following examples describe in detail methods of preparing crystalline 4-chloro-N-(4-(morpholinomethyl)phenyl)benzamide and crystalline 4-chloro-N-(4-(morpholinomethyl)phenyl)benzamide hydrochloride, properties of the crystalline compounds, and methods of using the crystalline compounds. It will be apparent to those skilled in the art that many modifications, both to materials and methods, may be practiced without departing from the scope of the invention.

Example 1

Synthesis of Crystalline
4-Chloro-N-(4-(morpholinomethyl)phenyl)benzamide
Hydrochloride 4-Chloro-N-(4-(morpholinomethyl)phenyl)benzamide from Example 2 (10 g, 0.03 moles) was suspended in tetrahydrofuran (250 mL, 25 vol). The suspension was stirred at room temperature for 10 min to obtain clear solution. The solution was cooled to from 0-5° C. and 4M HCl in 1,4-dioxane (7.5 L) was added over a period of 10 min. The obtained white suspension was stirred at room temperature for 2 hours and the solids filtered. The filtered solids were washed with tetrahydrofuran (20 mL, 2 vol) and the washed solids dried at 50° C. for 16 hours to provide the 4-chloro-N-(4-(morpholinomethyl)phenyl)benzamide hydrochloride salt (8.7 g, 78% yield) as a white, crystalline solid (HPLC purity: >99.5%); m/z calculated for $[M+H]^+$ 331.1, found 331.6. $^1$H-NMR (400 MHz, DMSO-d6) δ 11.45 (broad s, 1H), 10.50 (d, J=12 Hz, 1H), 8.01 (d, J=10.8 Hz, 2H), 7.86 (d, J=8.8 Hz, 2H), 7.60 (m, J=2.4 and 2.8 Hz, 4), 4.28 (d, J=5.2 Hz, 2H), 3.93 (m, J=12 Hz, 2H), 3.84 (m, J=8 Hz, 2H), 3.38 (m, J=8 Hz, 2H), 3.20 (m, J=12 Hz, 2H), 3.05 (m, 2H).

Example 2

Synthesis of Crystalline
4-Chloro-N-(4-(morpholinomethyl)phenyl)benzamide

Step A. Synthesis of 4-chloro-N-(4-(hydroxymethyl)phenyl)benzamide.

4-Amino benzyl alcohol (25 g, 0.203 moles) was suspended in ethyl acetate (250 mL, 10 vol.). To this suspension was added potassium carbonate (58.8 g, 0.426 moles). The suspension was cooled to from 0-5° C. and a solution of 4-chlorobenzoyl chloride (37.3 g, 0.213 moles) in ethyl acetate (50 mL, 2 vol) added. The pale-yellow suspension was allowed to warm to room temperature and stirred for 3 h. The progress of the reaction was monitored by TLC/HPLC.

After the reaction was complete, the reaction was quenched with water (125 mL, 5 vol) and the suspension stirred for 30 min at room temperature. The suspension was filtered and the solids washed with water (50 mL, 2 vol) followed by ethyl acetate (50 mL, 2 vol). The solids were dried at 50° C. to provide 4-chloro-N-(4-(hydroxymethyl)phenyl)benzamide (45.2 g, 87% yield) as a pale yellow solid (HPLC purity 99%).

Step B. Synthesis of 4-chloro-N-(4-(morpholinomethyl)phenyl)benzamide.

4-Chloro-N-(4-(hydroxymethyl)phenyl)benzamide (45 g, 0.171 moles, from step A) in dichloromethane (225 mL, 5.0 vol) was cooled to from 0-5° C. Thionyl chloride (30.6 g, 0.257 moles) was added dropwise to the cooled suspension. The suspension was warmed to room temperature and stirred for 3 hrs. The progress of the reaction was monitored by TLC.

After the reaction was complete, the suspension was concentrated at 45° C. to dryness to provide 4-chloro-N-(4-(chloromethyl)phenyl)benzamide. The dried product was washed twice with dichloromethane (135 mL, 3 vol). The washed product was diluted with dichloromethane (450 mL, 10 vol) and used in the next step.

4-Chloro-N-(4-(chloromethyl)phenyl)benzamide in dichloromethane was cooled to 0-5° C. Morpholine (44.9 g, 0.515 moles) was added dropwise to the cooled suspension over a period of 20 min. The resulting pale-yellow suspension was allowed to warm room temperature. The suspension was then stirred for 8 hours at 25-30° C. Progress of the reaction was monitored by TLC.

After the reaction was complete, the reaction was quenched with water (225 mL, 5.0 vol). The white suspension was stirred for 40 min at room temperature and the solids filtered. The solids were washed with dichloromethane (90 mL, 2 vol). The solids were added to water (225 mL, 5 vol) and stirred for 2 h at 20-25° C. The product, 4-chloro-N-(4-(morpholinomethyl)phenyl)benzamide (35 mg, 61/7% yield), was obtained as a white solid (HPLC purity 98.1%) and dried at 60±5° C. for 16 hours. $^1$H-NMR (400 MHz, DMSO-d6) δ 10.30 (s, 1H), 7.974 (d, 2H, J=8.8 H), 7.711 (d, 2H, J=8.4 Hz), 7.602 (d, 2H, J=8 Hz), 7.273 (d, 2H, J=8.4 Hz), 3.563 (m, 4H, J=4.4 Hz and 8.8 Hz), 3.41 (s, 2H), 2.31 (m, 4H).

Example 3

Properties of Crystalline Compound (1) and Crystalline Compound (2)

X-ray powder diffraction (XRPD) was performed using a Shimadzu Lab XRD-6100 instrument with a scintillation detector in continuous scan mode using a Cu/K-α (λ=1.5406 Å) source. The diffraction patterns were obtained over a scan range from 3° to 50° at a scan speed of 2 deg/min, a sampling pitch of 0.02 deg and a preset time of 0.6 sec. XRPD patterns for crystalline compound (1) and crystalline compound (2) are provided in FIGS. 1 and 3, respectively.

Differential scanning calorimetry (DSC) was performed using a Perkin Elmer DSC 4000 (version 13.2.1.0007) instrument over a temperature range from 30° C. to 400° C. at a heating rate of 4° C./min and a nitrogen flow rate of 80 mL/min, using a sample mass of 3.1 mg. The method was used to obtain the DSC curve for crystalline compound (1) presented in FIG. 2.

Example 4

Solubility of Crystalline Compound (1) and Crystalline Compound (2)

The equilibrium solubility of crystalline compound (1) and crystalline compound (2) was measured in various aqueous buffers. The pH 4.0 and pH 5.0 buffers were prepared by combining 50 mL of 0.2 M potassium biphthalate with 150 mL of $H_2O$, and then adjusting to pH 4.0 or pH 5.0 with 10 N HCl. The pH 6.0 buffer was prepared by combining 50 mL of 0.2 M $KH_2PO_4$ with 150 mL of $H_2O$, and then adjusting to pH 6.0 with 10 N NaOH. The pH 7.4 buffer was prepared by combining 50 mL of 0.2 M $KH_2PO_4$ with 150 mL of $H_2O$, and then adjusting to pH 7.4 with 10 N NaOH. At least 1 mg of powder for each compound was combined with 1 mL of each buffer to make a saturated mixture. The samples were shaken overnight on a Thermomixer® at room temperature. The samples were then passed through a 0.45 m PTFE syringe filter. The filtrate was sampled and diluted in duplicate as appropriate into a mixture of 1:1 buffer:acetonitrile (ACN) prior to analysis. All samples were assayed by LC-MS/MS using electrospray ionization against standards prepared in a mixture of 1:1 assay buffer:ACN.

Standard concentrations ranged from 1.0 μM to 0.3 nM.

The samples were analyzed by LCMS using a Waters Acuity® UPLC BEH Phenyl 30×2.1 mm, 1.7 μm liquid chromatography column and a PE Sciex® API 4000 mass spectrometer equipped with a Turbo Ionspray.

The aqueous solubility of crystalline compound (1) and crystalline compound (2) is provided in Table 1.

TABLE 1

| Aqueous solubility of crystalline compounds (1) and (2). | | | | |
|---|---|---|---|---|
| | Solubility (μM) | | | |
| Compound | pH 4.0 | pH 5.0 | pH 6.0 | pH 7.4 |
| Crystalline Compound (1) | 12,500 | 10,250 | 8,165 | — |
| Crystalline Compound (2) | $^1$— | — | — | 12.5 |

$^1$ Not measured.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A compound, crystalline 4-chloro-N-(4-(morpholinomethyl)phenyl)benzamide hydrochloride:

wherein the compound is characterized by an XRPD pattern comprising characteristic diffraction peaks at least at 10.8±0.2°, 18.2°±0.2°, 14.8°±0.2°, 19.9±0.2°, 22.0±0.2°, 22.5±0.2°, 23.2±0.2°, 23.9±0.2°, 27.3±0.2°, 28.0±0.2°, and 29.2±0.2° expressed as 2θ angles and determined using Cu-Kα radiation.

2. The compound of claim 1, wherein the compound is characterized by an XRPD pattern comprising characteristic diffraction peaks at least at 10.8°±0.1°, 18.2°±0.1°, 14.8°±0.1°, 19.9±0.1°, 22.0±0.1°, 22.5±0.1°, 23.2±0.1°, 23.9±0.1°, 27.3±0.1°, 28.0±0.2°, and 29.2±0.2° expressed as 2θ angles and determined using Cu-Kα radiation.

3. The compound of claim 1, wherein the compound is characterized by an XRPD pattern as shown in FIG. 1.

4. The compound of claim 1, wherein the compound has an endothermic onset temperature from 220° C. to 230° C., where the endothermic onset temperature is determined by differential scanning calorimetry.

5. The compound of claim 1, wherein the compound has an endothermic peak from 235° C. to 245° C., wherein the endothermic peak is determined by differential scanning calorimetry.

6. The compound of claim 1, wherein the compound has an endothermic enthalpy from 52 J/g to 62 J/g, wherein the endothermic enthalpy is determined by differential scanning calorimetry.

7. The compound of claim 1, wherein the compound has an exothermic onset temperature from 292° C. to 302° C., wherein the exothermic onset temperature is determined by differential scanning calorimetry.

8. The compound of claim 1, wherein the compound has an exothermic peak from 310° C. to 320° C., wherein the exothermic peak is determined by differential scanning calorimetry.

9. The compound of claim 1, wherein the compound has an exothermic enthalpy from 122 J/g to 132 J/g, wherein the exothermic enthalpy is determined by differential scanning calorimetry.

10. The compound of claim 1, wherein the compound exhibits a differential scanning calorimetry curve as shown in FIG. 2.

11. A pharmaceutical composition comprising the compound of claim 1 and a pharmaceutically acceptable excipient.

12. The pharmaceutical composition of claim 11, wherein the pharmaceutical composition comprises a therapeutically effective amount of the compound for treating a disease in a patient, wherein the disease is selected from acute lung injury, acute respiratory distress syndrome, and chronic obstructive pulmonary disease.

13. A compound, crystalline 4-chloro-N-(4-(morpholinomethyl)phenyl)benzamide hydrochloride:

wherein the compound exhibits a differential scanning calorimetry curve as shown in FIG. 2.

14. A pharmaceutical composition comprising the compound of claim 13 and a pharmaceutically acceptable excipient.

15. The pharmaceutical composition of claim 14, wherein the pharmaceutical composition comprises a therapeutically effective amount of the compound for treating a disease in a patient, wherein the disease is selected from acute lung injury, acute respiratory distress syndrome, and chronic obstructive pulmonary disease.

* * * * *